United States Patent [19]

Smith

[11] Patent Number: 5,350,756

[45] Date of Patent: Sep. 27, 1994

US005350756A

[54] USE OF A CYTOCHROME OXIDASE INHIBITOR TO INCREASE THE COUGH-SUPPRESSING ACTIVITY OF DEXTROMORPHAN

[76] Inventor: Richard A. Smith, 7569 Cabrillo Ave., La Jolla, Calif. 92037

[21] Appl. No.: 890,432

[22] Filed: May 28, 1992

Related U.S. Application Data

[63] Continuation-in-part of Ser. No. 717,424, Jun. 17, 1991, Pat. No. 5,166,207.

[51] Int. Cl.$^5$ ............................................. A61K 31/44
[52] U.S. Cl. ................................... 514/289; 514/295; 514/305
[58] Field of Search ................ 514/295, 289, 305, 270

[56] References Cited

U.S. PATENT DOCUMENTS 5,166,207 11/1992 Smith .................................. 514/270

OTHER PUBLICATIONS

Koppel, C., et al, "Urinary metabolism of dextromethorphan in man," *Arzneim.-Forsch./Drug Research* 37: 1304–1306 (1987).

Guttendorf, R. J., et al, "Simplified phenotyping with dextromethorphan by thin-layer chromatography," *Ther. Drug. Monit.* 10: 490–498 (1988).

Kupfer, A., et al "Dextromethorphan as a safe probe for debrisoquine hydroxylation polymorphism," *Lancet ii:* 517–518 (1984).

*Physician's Desk Reference*, 44th Edition (1988), pp. 670–671 (Medical Economics Company, 1990).

Inaba, T., et al, "In vitro inhibition studies of two isozymes of human liver cytochrome P-450," *Drug Metabolism and Disposition* 13: 443–447 (1985).

Inaba, T., et al, "Quinidine: Potent inhibition of sparteine and debrisoquin oxidation in vivo," *Br. J. Clin. Pharmacol.* 22: 199–200 (1986).

Broly, F., et al, "Effect of quinidine on the dextromethorphan O-methylase activity of microsomal fractions from human liver," *Br. J. Clin. Pharmacol.* 28: 29–36 (1989).

Broly, F., et al, "Inhibitory studies of mexiletine and dextromethorphan oxidation in human liver microsomes," *Biochem. Pharmacol.* 39: 1045–1053 (1990).

Brinn, R., et al, "Sparteine oxidation is practically abolished in quinidine-treated patients," *Br. J. Clin. Pharmacol.* 22: 194–197 (1986).

Brosen, K., et al, "Extensive metabolizers of debrisoquin become poor metabolizers during quinidine treatment," *Pharmacol. Toxicol.* 60: 312–314 (1987).

Nielsen, M. D., et al, "A dose-effect study of the in vivo inhibitory effect of quinidine on sparteine oxidation in man," *Br. J. Clin. Pharmacol.* 29: 299–304 (1990).

Walker, E. O., and Hunt, V. P., "An open label trial of dextromethorphan in Huntington's Disease," *Clin. Neuropharmacol.* 12: 322–330 (1989).

Albers, G. W., et al, "Safety and tolerance of oral dextromethorphan in patients at risk for brain ischemia," *Stroke* 22: 1075–1077 (1991).

Applebaum, J. S., et al, "Dextromethorphan in the treatment of ALS: A pilot study," Abstract No. 960S (p. 393) in *Neurology* 41 (Suppl. 1), Mar. 1991.

*Primary Examiner*—Marianne M. Cintins
*Assistant Examiner*—T. J. Criares
*Attorney, Agent, or Firm*—Patrick D. Kelly

[57] ABSTRACT

This invention discloses a method for increasing the effectiveness of dextromethorphan (DM) as an antitussive agent (i.e., as a cough suppressant). This method involves the concurrent administration of DM and a second agent which inhibits the oxidative activity of debrisoquin hydroxylase, a cytochrome P450 oxidase enzyme. Effective anti-oxidant compounds include quinidine, yohimbine, and fluoxetine.

6 Claims, 2 Drawing Sheets

DEGRADATION OF DEXTROMETHORPHAN

USE OF A CYTOCHROME OXIDASE INHIBITOR TO INCREASE THE COUGH-SUPPRESSING ACTIVITY OF DEXTROMORPHAN

RELATED APPLICATION

This is a continuation-in-part of a prior U.S. application Ser. No. 717,424, filed on Jun. 17, 1991, now U.S. Pat. No. 5,166,207.

BACKGROUND OF THE INVENTION

This invention relates to pharmacology, and to the use of dextromethorphan as a cough suppressant.

Dextromethorphan (frequently abbreviated as DM) is the common name for (+)-3-methoxy-N-methylmorphinan. It widely used as a cough syrup, and is described in references such as Rodd 1960 (full citations to articles are provided below) and Goodman and Gilman's *Pharmacological Basis of Therapeutics*. Briefly, DM is a non-addictive opioid comprising a dextrorotatory enantiomer (mirror image) of the morphinan ring structure which forms the molecular core of most opiates.

The cough-suppressing activity of DM is believed to be due primarily to its activity at a class of neuronal receptors known as sigma receptors. These are often referred to as sigma opiate receptors, but there is some question as to whether they are opiate receptors, so many researchers refer to them simply as sigma receptors, or as high-affinity dextromethorphan receptors. They are inhibitory receptors, which means that their activation by DM or other sigma agonists causes the suppression of certain types of nerve signals, apparently including the signals that mediate coughing.

Dextromethorphan also acts at another class of receptors known as N-methyl-D-aspartate (NMDA) receptors, which are one type of excitatory amino acid (EAA) receptor. Unlike its agonist activity at sigma receptors, DM acts as an antagonist at NMDA receptors, which means that DM suppresses the transmission of nerve impulses mediated via NMDA receptors. Since NMDA receptors are excitatory receptors, the activity of DM as an NMDA antagonist also leads to the suppression of certain types of nerve signals, which may also be involved in some types of coughing.

Due to its activity as an NMDA antagonist, DM and one of its metabolites, dextrorphan, are being actively evaluated as possible treatments for certain types of excitotoxic brain damage caused by ischemia (low blood flow) and hypoxia (inadequate oxygen supply), which are caused by events such as stroke, cardiac arrest, and asphyxia. The anti-excitotoxic activity of dextromethorphan and dextrorphan, and the blockade of NMDA receptors by these drugs, are discussed in items such as Choi 1987, Wong et al 1988, Steinberg et al 1988, and U.S. Pat. No. 4,806,543 (Choi 1989).

Dextromethorphan has also been reported to suppress activity at neuronal calcium channels (Carpenter et al 1988).

Dextromethorphan and the receptors it interacts with are further discussed in Tortella et al 1989, Leander 1989, Koyuncuoglu & Saydam 1990, Ferkany et al 1988, George et al 1988, Prince & Feeser 1988, Feeser et al 1988, Craviso and Musacchio 1983, and Musacchio et al 1988.

Because of its activity as an NMDA antagonist which may be able to block excitotoxic damage to neurons, DM has become of interest as a potential therapy to treat progressive neurodegenerative diseases, including Parkinson's disease, Alzheimer's disease, and amyotrophic lateral sclerosis (ALS, also called Lou Gehrig's disease), all of which are suspected of containing an excitotoxic aspect of their etiology. Accordingly, the Applicant, a neurologist who specializes in working with ALS patients, undertook a study of DM to determine whether it might be able to retard the progress of ALS.

Regrettably, DM was not able to slow down the progressive loss of strength, slurring of speech, and other muscular symptoms suffered by those patients. However, during the course of that study, other important findings emerged, as discussed below.

Dextromethorphan Metabolism

Before the study began, the Applicant was aware that in most people, DM disappears fairly rapidly from the bloodstream (see, e.g., Vetticaden et al 1989 and Ramachander et al 1977). DM is converted in the liver to two metabolites called dextrorphan and 3-methoxymorphinan, by an enzymatic process called O-demethylation; in this process, one of the two pendant methyl groups is replaced by hydrogen. If the second methyl group is removed, the resulting metabolite is called 5-hydroxymorphinan. Dextrorphan and 5-hydroxymorphinan are covalently bonded to other compounds in the liver (primarily glucuronic acid or sulfur-containing compounds such as glutathione) to form glucuronide or sulfate conjugates which are eliminated fairly quickly from the body via urine. These metabolic pathways are shown in FIG. 1.

During his initial studies with ALS patients, the Applicant confirmed that the same process of rapid oxidation and elimination occurs in such patients. No difference in the metabolism of dextromethorphan was detected in ALS patients compared to previously reported data for healthy adults.

The rapid metabolism of DM makes it very difficult to correlate DM quantities administered to a patient, with DM quantities circulating in the patient's blood. Since the Applicant wanted to stabilize blood concentrations of DM in order to improve the significance and reliability of any results in ALS patients, he did a literature search on the metabolic pathways that cause DM to disappear from the bloodstream. That search quickly identified a particular enzyme that is primarily responsible for DM oxidation. This enzyme is usually referred to as debrisoquin hydroxylase, since it was discovered a number of years ago to carry out a hydroxylation reaction on debrisoquin. It is also referred to in various articles as $P450_{DB}$ or P450-2D6. It apparently is identical to an enzyme called sparteine monooxygenase, which was shown years ago to metabolize sparteine; it was not until recently that scientists realized that a single isozyme appears to be primarily responsible for oxidizing both debrisoquin and sparteine, as well as dextromethorphan and various other substrates.

Debrisoquin hydroxylase belongs to a family of enzymes known as "cytochrome P-450" enzymes, or as "cytochrome oxidase" enzymes. These enzymes are found at high concentrations in liver cells (primarily in microsomes, which are organelles inside the liver cells), and at lower concentrations in various other organs and tissues such as the lungs; see, e.g., Fonne-Pfister et al 1987 and Niznik et al 1990. By oxidizing lipophilic compounds, cytochrome oxidase enzymes help eliminate compounds that would otherwise act as toxins or accumulate to undesired levels. This oxidation renders lipophilic compounds more soluble in water, which helps the body eliminate them in urine or in aerosols exhaled out of the lungs.

A follow-up literature search by the Applicant revealed that a number of compounds inhibit the activity of the debrisoquin hydroxylase (sparteine monooxygenase) isozyme; see Inaba et al 1985. The most powerful of these inhibitors is quinidine, a dextrorotatory stereoisomer of quinine; it is normally used to treat cardiac arrhythmias. Inaba et al 1986 and Nielsen et al 1990 discuss the ability of quinidine to inhibit the oxidation of sparteine in in vivo animal tests, and Brinn et al 1986, Brosen et al 1987, and Broly et al 1989 discuss the ability of quinidine to inhibit DM metabolism in liver cell preparations. After studying the Inaba et al 1985 article, which rated quinidine as the most potent inhibitor of the sparteine monooxygenase enzyme, and after recognizing that the sparteine monooxygenase enzyme appears to be the same enzyme referred to elsewhere as debrisoquin hydroxylase, the Applicant realized that quinidine might be a useful adjunct for co-administration along with DM, in order to prolong the life and increase the concentration of DM in the circulating blood. When he tested that hypothesis, using quinidine in conjunction with DM (both administered orally), the Applicant discovered that quinidine does indeed have a pronounced effect in increasing and stabilizing the quantity of DM circulating in the blood. That discovery is discussed in more detail in the parent application cited above, Ser. No. 717,424.

The Applicant also discovered that DM in conjunction with quinidine had a remarkable and unexpected side effect: it was highly effective in reducing the symptoms of "emotional lability" in several ALS patients who were involved in the test. Emotional lability is a complex problem in which patients suffering from bilateral neurological damage (typically due to a stroke or head injury or a neurologic disease such as ALS or Alzheimer's disease) become unable to control spasmodic emotional outbursts such as explosive laughing or uncontrollable weeping. In patients suffering from brain damage leading to emotional lability, such outbursts often occur at highly inappropriate times and without provocation. They make it very difficult for such patients to go out in public or interact comfortably with friends and family, and they often generate severe feelings of self-directed anger, inadequacy, and depression.

The ability of DM in conjunction with quinidine to control emotional lability is discussed in a separate patent application. This unexpected beneficial effect was not observed in any patients who received DM alone. All patients who became involved in the study initially received DM by itself at the beginning of their participation in the study, to ensure that DM would not adversely affect them. Quinidine was added to the treatment regime only after a tolerance and dosage range for DM had been established for a patient, and the benefits of DM in suppressing emotional lability did not become apparent until after a patient also began taking quinidine.

This unexpected discovery caused the Applicant to focus even more attention on the combination of DM and quinidine. During a careful study of the prior art, a question repeatedly occurred to him: since quinidine and certain other anti-oxidant drugs have been shown in the prior art to suppress the metabolism of dextromethorphan, why hadn't anyone else ever administered quinidine or other anti-oxidants as a way to increase DM concentrations in the blood of patients being treated with DM?

The answer to that question emerged when several previously unrelated facts were correlated:

1. A substantial fraction of the general public (roughly 7 to 10%) does not have a properly functioning gene which encodes the debrisoquin hydroxylase enzyme.

2. People who do not have the properly functioning debrisoquin hydroxylase enzyme are classified and referred to by doctors and pharmacologists as "poor metabolizers." Such patients are regarded as somewhat high-risk patients who must be treated with special care and attention, since they are overly sensitive to certain drugs that can be prescribed safely to people who have the full set of cytochrome P450 enzymes (such people are usually referred to as "extensive metabolizers" or "good metabolizers").

3. In addition to the inhibition of debrisoquin hydroxylase, which is exceptionally potent and easily demonstrated, other cytochrome P450 isozymes are also likely to be suppressed by quinidine, with varying levels of binding affinity. Cytochrome P-450 enzymes are notoriously non-specific; a single isozyme can react with numerous substrates having widely different chemical structures, and various isozymes are known to have overlapping activity on a single substrate. This is consistent with their role in eliminating lipophilic toxins, and it is illustrated by the ability of debrisoquin hydroxylase to metabolize numerous different substrates, including dextromethorphan, debrisoquin, and sparteine (which have very different structures). Accordingly, even though quinidine exerts its most marked effect on debrisoquin hydroxylase, it is likely to suppress a number of other cytochrome P450 enzymes as well, thereby subjecting a patient to a more general loss of normal and desirable liver activity.

4. Since DM is a relatively safe drug which can be administered without a prescription, it can be used as a convenient tool (often called a probe drug) during clinical tests to determine whether a patient is a good metabolizer or a poor metabolizer. Such diagnostic tests are performed so that a patient who is a "poor metabolizer" can be identified and protected against various drugs which he or she cannot metabolize properly.

Some of the foregoing points are documented in articles such as Guttendorf et al 1988, Kupfer et al 1984, and Koppel et al 1987, which discuss poor metabolizers; other points were gleaned from other articles, cited above, which discuss the general characteristics of cytochrome P450 enzymes.

In light of these facts and correlations, reports such as Broly et al 1989, which indicates that quinidine suppresses DM oxidation in liver cell preparations, are actually warnings calling attention to the fact that if a patient is taking quinidine, the patient becomes a high-risk "poor metabolizer" who must be protected against the dangers that affect poor metabolizers. In addition, these articles warn doctors that if a patient is taking a drug such as quinidine, then the diagnostic test for identifying "poor metabolizers" will not give accurate results and should not be used.

The Applicant's analysis of the literature also disclosed another important factor. The primary oxidized metabolic product of dextromethorphan is dextrorphan, which is widely believed among neurologists to be active in exactly the same manner as dextromethorphan; both drugs reportedly are sigma agonists, NMDA antagonists, and calcium channel antagonists. Since the metabolite of DM is widely believed to have exactly the same neuronal activities as DM, neurologists and others have had no apparent motivation to try to use anti-oxidants to increase DM concentrations in the blood.

As further evidence of the absence of any interest among neurologists in using cytochrome P450 inhibitors to increase dextromethorphan concentrations in the blood of patients receiving DM, it should be noted that a number of recent studies have been performed to evaluate DM in patients suffering neurological diseases (e.g., Walker and Hunt 1989, Albers et al 1991, and Applebaum et al 1991). Although all of these researchers clearly recognize the problem of rapid DM metabolism, none of their reports made any mention whatever of using quinidine or any other oxidation inhibitor in combination with DM, to slow down the metabolic degradation of DM.

Despite the relevant facts and prevailing beliefs in this field of research, the work by the Applicant has disclosed that co-administration of quinidine in conjunction with DM leads to an important therapeutic benefit (i.e., the suppression of emotional lability, as discussed above). This benefit was clear and remarkably effective in patients treated with both drugs, but it was not detectable in any of the patients when they were treated with dextromethorphan alone.

In summary, the Applicant has discovered and demonstrated two things in clinical trials:

(1) the administration of a compound which inhibits debrisoquin hydroxylase, in conjunction with DM, causes a major increase in the concentration and stability of DM in the blood of patients, compared to patients who receive only DM; and, (2) the administration of a debrisoquin hydroxylase inhibitor in conjunction with DM has a clear and substantial impact on the detectable effects of DM in humans.

These facts form the basis of the subject invention. Since the co-administration of a debrisoquin hydroxylase inhibitor concurrently with DM substantially increases the observable therapeutic effects of DM in human clinical trials, then the effectiveness of DM as an antitussive agent (i.e., as a cough suppressant) can also be increased by the co-administration of a cytochrome oxidase inhibitor.

Accordingly, one object of the subject invention is to disclose that dextromethorphan, when co-administered with a cytochrome P450 inhibitor such as quinidine, is more effective than DM by itself in suppressing coughs.

Another object of the subject invention is to disclose a method of treating severe and chronic coughing.

These and other objects of the invention will become apparent from the following description of the invention.

SUMMARY OF THE INVENTION

This invention discloses a method for increasing the effectiveness of dextromethorphan (DM) as an antitussive agent (i.e., as a cough suppressant). This method involves the co-administration of DM along with a second agent which inhibits the oxidative activity of debrisoquin hydroxylase, such as quinidine, yohimbine, or fluoxetine.

DETAILED DESCRIPTION OF THE PREFERRED EMBODIMENTS

Figure 1:
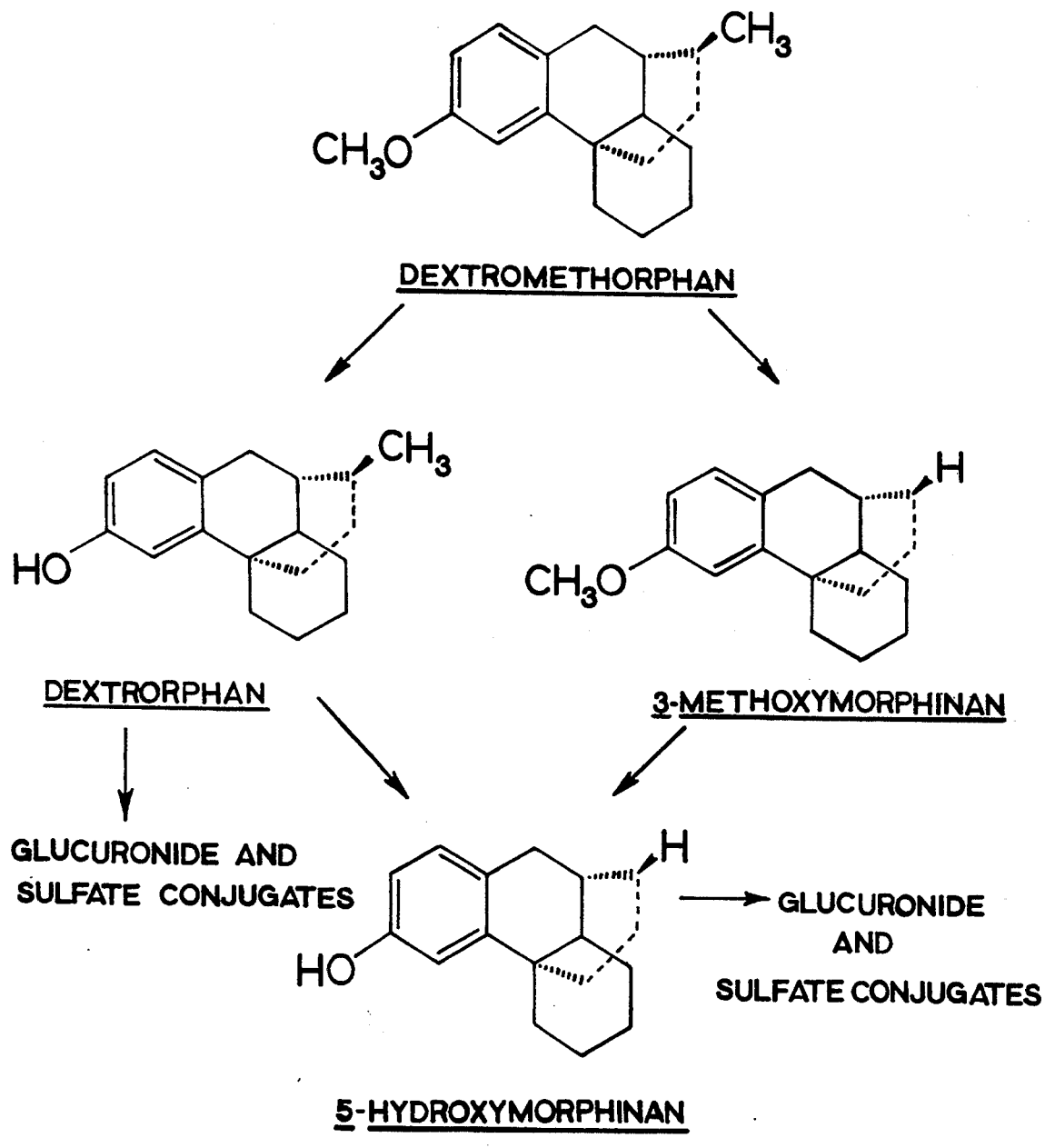
FIG. 1 is a depiction of the metabolic pathways that lead to the degradation and elimination of dextromethorphan.

This invention discloses a method for increasing the effectiveness of dextromethorphan (DM) as an antitussive agent (i.e., as a cough suppressant). This method involves the co-administration of DM along with a second agent (such as quinidine) which inhibits the oxidative activity of the debrisoquin hydroxylase enzyme, which is one isozyme in the cytochrome P-450 family. By inhibiting the enzymatic degradation and elimination of DM, the anti-oxidant compound increases, stabilizes, and prolongs the concentration of DM in the circulating blood, as demonstrated in the Examples below.

The quinidine-mediated increase of DM concentration in the blood of a patient will directly increase the ability of DM to carry out functions which directly depend on the concentration of DM in the blood. As discussed in the Background section, the activity of DM in suppressing nerve signals is believed to involve at least two and possibly more types of neuronal receptor; DM functions acts as an agonist at sigma receptors, which are inhibitory, and as an antagonist at NMDA receptors, which are excitatory, and it may also function to suppress nerve impulses mediated by various other neuronal mechanisms, such as calcium channels. All of these neuronal interactions involve direct contact of DM molecules with neurons.

Accordingly, an increase in the concentration of DM in the blood will increase the ability of DM to exert its neuronal effects, which include the suppression of coughing. This generalization, in its broadest form, may be limited by a "ceiling effect" at which DM may exert maximal effects which cannot be increased even if more DM is added to the system; in particular, it has been shown that DM, when administered at massive doses in an effort to protect cells against ischemic damage in in vitro models of stroke, does indeed encounter a ceiling effect. However, the ceiling effect involved in massive doses used in stroke research is not approximated or even approached when DM is administered at dosages used for suppressing coughs. In the dosages typically used to treat coughs, the blood levels of DM in roughly 90% of the general public is either extremely low or undetectable.

Dextromethorphan is widely available in cough syrup formulations, at dosages up to about 120 mg/day for an adult, without a prescription. It is also available in pills, but only by prescription. This invention anticipates DM dosages in the range of about 20 mg/day to about 200 mg/day, depending on factors such as the weight of the patient, the severity of the cough, and the potency and dosage of the anti-oxidant agent used in conjunction with DM.

Currently, quinidine is available only by prescription; in addition to being a relatively powerful heart medicine, it also converts people with normal metabolism into so-called "poor metabolizers" as described in articles such as Kupfer et al 1984 and Guttendorf et al 1988.

Accordingly, the drug combination disclosed herein is currently anticipated for prescription only under the supervision of a physician, and it preferably should be used for treating severe and/or chronic coughing that cannot be adequately treated by dextromethorphan alone, such as in patients suffering from pulmonary or bronchial disease or other severe distress.

However, it should also be recognized that the dosage of quinidine which provides a major increase in DM concentration in the blood are only a fraction of the dosages normally used for anti-arrhythmic action. Quinidine dosages of 600-1200 mg/day are commonly taken by cardiac patients; by contrast, dosages of only 150 mg/day are effective in increasing DM concentrations, and it is believed by the Applicant that even lower dosages (such as 50 mg/day) will be effective in at least some patients. Accordingly, a combination of DM in an antitussive dosage and a relatively small quantity of quinidine (or a somewhat less potent oxidation inhibitor, as discussed below) may be safe enough for over-the-counter sale. In view of the fact that contagious diseases are often spread by coughing, optimal public benefit might be achieved by making a combination of DM and an oxidation inhibitor available over-the-counter to anyone suffering from a severe cough, in a "maximum strength" formulation.

Regardless of how it is sold, people using this drug combination should be warned that oxidation inhibitors suppress the body's ability to metabolize and eliminate certain types of drugs. Accordingly, anyone taking an oxidant inhibitor should be generally advised to discontinue the consumption of alcohol and other non-essential drugs, or drugs that suppress liver functioning. In addition, physicians prescribing anti-oxidants should be alerted of potential interactions between anti-oxidants and other drugs, such as certain types of anticoagulants.

As mentioned above, a number of drugs have been identified as being effective in inhibiting debrisoquin hydroxylase. Such drugs include nortriptyline, chlorpromazine, domperidone, haloperidol, pipamperone, labetalol, metaprolol, oxprenolol, propranolol, timolol, mexiletine, quinine, diphenhydramine, ajmaline, lobeline, papaverine, and yohimbine. Compounds which are relatively potent include yohimbine, haloperidol, ajmaline, lobeline, and pipamperone; these drugs reportedly have Michaelis-Menton inhibition ($K_i$) values ranging from 0.33 to 4, compared to a $K_i$ value of 0.06 for quinidine; see Inaba et al 1985.

In addition, research by the Applicant has also indicated that fluoxetine (sold under the trade name Prozac) is effective in increasing DM concentrations in the blood.

Since the compounds listed above are less potent than quinidine in inhibiting debrisoquin hydroxylase, they may be preferred for use by some patients or doctors, since they are likely to have less effect in causing patients to become "poor metabolizers" as described in articles such as Guttendorf et al 1988, Kupfer et al 1984, and Koppel et al 1987.

Additionally or alternately, a doctor can determine an optimal dosage of both quinidine and dextromethorphan for a specific patient who is being treated for chronic and/or severe coughing, by means of administering various dosages of each and subsequently (1) analyzing blood samples to determine the concentration of DM in the circulating blood, using techniques such as described in Example 2, and/or (2) evaluating the patient's progress to determine which combination of dosages provides the best result in effectively suppressing coughing.

During the tests on ALS patients, minor to moderate side effects (such as drowsiness or fatigue, lightheadedness, or loss of appetite) were reported by several patients. A small percentage of the patients who received both drugs over a prolonged time suffered severe side effects; in addition, one person was allergic to quinidine. Despite those problems in a few patients, the large majority of patients and controls reported no adverse side effects.

EXAMPLES

Since the research that led to this invention was done by a neurologist who was initially interested in finding out whether DM might be able to retard the progress of ALS, the studies described herein were done on patients suffering from ALS, most of whom are adults more than 50 years old. No differences were detected in the metabolism of DM in ALS patients, compared to reported findings involving adults who do not have ALS, or to one-day tests involving healthy volunteers as a control population.

Example 1

Urinary DM/DR Ratios

Six patients suffering from ALS were administered orally a single 60 mg dextromethorphan dose. Several hours later, a urine sample was collected, and the urine concentrations of dextromethorphan (DM) and dextrorphan (DR) were measured as described below to determine a DM/DR ratio. A low DM/DR ratio indicates that DM is being rapidly oxidized to the DR metabolite in that body of that patient. In a different week, 60 mg of DM and 150 mg of quinidine were orally administered to the same patients, and urinary DM and DR levels and DM/DR ratios were determined again.

DM and DR urinary levels without quinidine were determined by adding 40 mg of thebaine as an internal standard to 1 mL of urine. To this was added 2000 units of beta-glucuronidase in 1 mL of acetate buffer (0.1M, pH 5.0). The mixture was incubated for 18 hours at 37° C. and then extracted by adding 1 mL of phosphate buffer (pH 12, 0.10M) and 7 mL of n-butanol/hexane (10:90 v/v). After mixing and centrifugation, the organic layer was transferred to a clean tube, acidified with 400 uL of 0.01N HCL and 20 microliters (uL) of aqueous phase injected into a high performance liquid chromatography (HPLC) system. The HPLC used a phenyl column equilibrated with a mobile phase of acetonitrile:water (51:49, v/v) containing 10 mM $KHPO_4$, 10 mM hexane sulfonic acid, pH 4.0 (flow rate 1.2 mL/min). Detection of thebaine, dextromethorphan and dextrorphan was achieved by fluorescence (Kratos FS-980 Fluorometer) with an excitation wavelength of 228 nm and no emission cutoff filter.

A gas chromatograph/mass spectroscopy (gc/ms) assay was employed for determining dextromethorphan and dextrorphan levels in the presence of quinidine. Briefly, 0.5 ml urine samples were spiked with 500 nanograms (ng) of dimethacrine. The urine pH was adjusted to 5.0 with 0.1M acetate buffer (usually about 1.0 ml), and beta-glucuronidase was added (2000 units/ml urine). The mixture was incubated and shaken at 37° C. for 18 hours. The urine was subsequently adjusted to pH 10-11 with 1.0 mL of phosphate buffer and the urine extracted with 5 mL of dichloromethane. The dichloromethane extract was evaporated under nitrogen, reconstituted in 300 uL of BSTFA and injected onto a gc-ms analyzer equipped with a capillary SE-30 column. Gas chromatographic conditions were: injector and transfer line temperature 250° C., oven 70° C. to 260° C. at 20° C. per minute, and source temperature 180° C. Detection was by selected ion monitoring at m/z 271 for dextromethorphan, 294 for the internal standard, and 329 for dextrorphan. Typical standard curves for dextromethorphan and dextrorphan were provided. Assay sensitivity was 100 ng/ml for dextromethorphan and 400 ng/ml for dextrorphan.

The results, in Table 1, indicate that quinidine is a potent inhibitor of dextromethorphan metabolism. The DM/DR ratio in all test subjects was increased by at least 2 and usually more than 3 orders of magnitude.

TABLE 1

| | URINARY DM/DR RATIOS | |
|---|---|---|
| Patient # | DM/DR Ratio, no quinidine | DM/DR Ratio, 150 mg quinidine |
| 1 | 0.0048 | 4.090 |
| 2 | 0.0220 | 3.460 |
| 3 | 0.0002 | 0.635 |
| 4 | 0.0003 | 0.420 |
| 5 | <0.0002 | 0.631 |
| 6 | 0.054 | 3.29 |

Followup tests were done on more than 50 people, including ALS patients and healthy controls who volunteered for one-day tests. The ALS patients received DM and quinidine on a daily basis over several weeks, while control subjects received only a single dose of each drug. The results were very similar to the data contained in Table 1.

Example 2

Plasma Concentrations of DM

Five patients were orally administered 120 mg of DM, with no co-administration of quinidine. Between 10 and 12 hours later, blood was sampled, blood plasma was isolated by centrifugation, and the plasma was analyzed to determine the DM concentration using the thebaine/HPLC method.

During a different week, the same patients were orally administered 60 mg of DM (half the control dosage) and 150 mg of quinidine. Between 10 and 12 hours later, blood was sampled and the plasma was analyzed for DM using thebaine/HPLC.

The results, in Table 2, indicate that quinidine causes a major increase in the concentration of DM in the blood plasma.

TABLE 2

| | Effects of 150 mg/day quinidine on plasma dextromethorphan levels | | |
|---|---|---|---|
| PATIENT | DEXTRO-METHORPHAN DOSE | DEXTRO-METHORPHAN PLASMA LEVEL | QUINIDINE DOSE (MG/DAY) |
| 1 | 120 MG/DAY | NOT DETECTABLE | 0 |
| | 60 MG ONCE | 33 NG/ML | 150 |
| 2 | 120 MG/DAY | 9.3 NG/ML | 0 |
| | 60 MG ONCE | 29.7 NG/ML | 150 |
| 3 | 120 MG/DAY | NOT DETECTABLE | 0 |
| | 60 MG ONCE | 29.0 NG/ML | 150 |
| 4 | 120 MG/DAY | 16.5 NG/ML | 0 |
| | 60 MG ONCE | 28.8 NG/ML | 150 |
| 5 | 120 MG/DAY | 6.05 NG/ML | 0 |

TABLE 2-continued

| | Effects of 150 mg/day quinidine on plasma dextromethorphan levels | | |
|---|---|---|---|
| PATIENT | DEXTRO-METHORPHAN DOSE | DEXTRO-METHORPHAN PLASMA LEVEL | QUINIDINE DOSE (MG/DAY) |
| | 60 MG ONCE | 45.6 NG/ML | 150 |

Subsequently, plasma levels were determined for about 15 other ALS patients who received dextromethorphan and quinidine over a prolonged period of time. The results were very similar to the data in Table 2.

Example 3

Dose-Response Study

Figure 2:
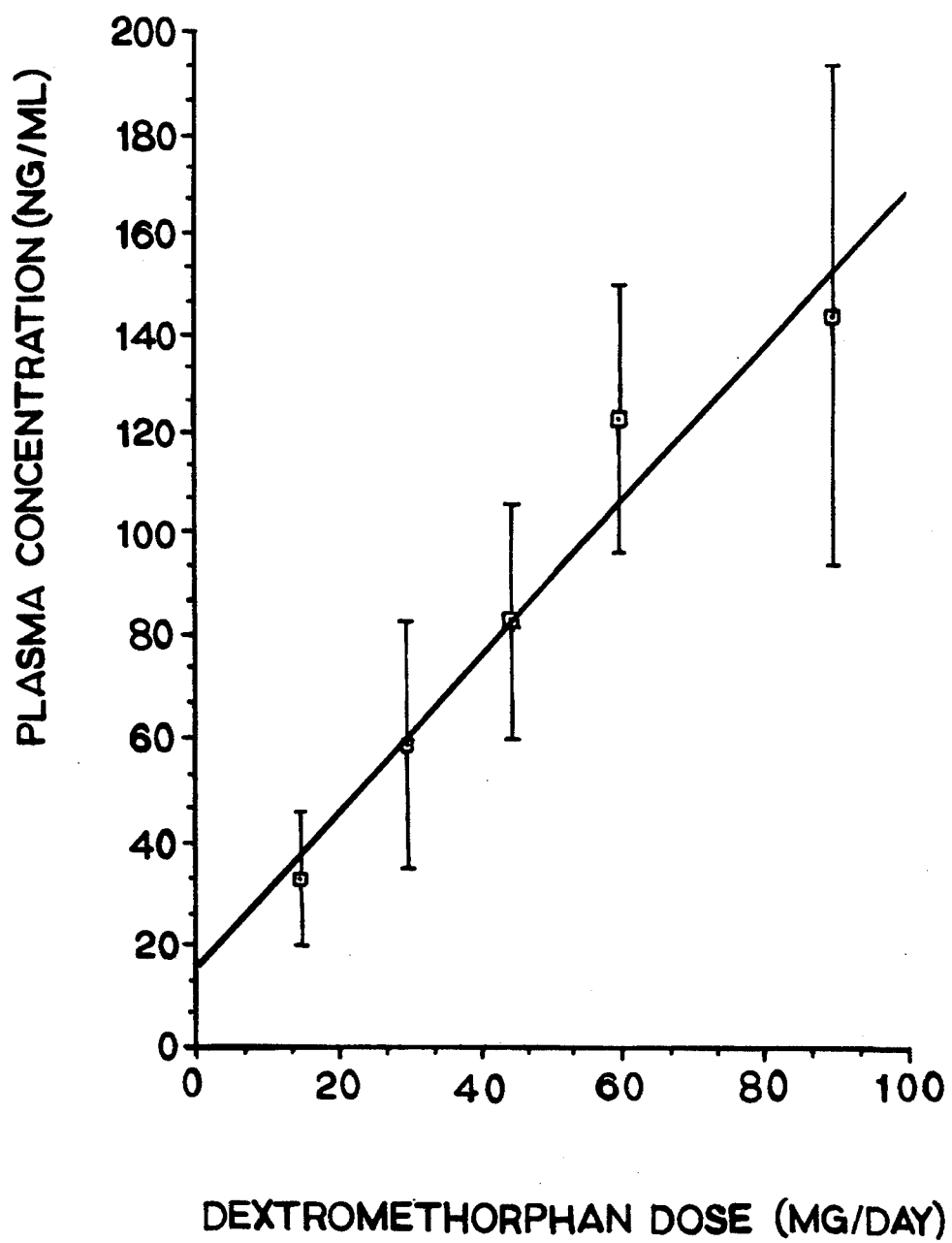
FIG. 2 is a graph depicting the relationship between DM oral dosages and DM plasma concentrations in patients receiving 150 mg/day of quinidine.

Additional studies were undertaken using a range of dosages of DM to establish a dose-response curve that correlates the quantity of DM orally administered to a patient with plasma concentrations 10 to 12 hours later (determined as described in Example 2). All patients received 150 mg of quinidine daily. The results of those studies are shown in graphical form in FIG. 2, with mean values shown as open squares and standard deviation ranges shown by vertical bars. The ascending line through the median values is a linear approximation; a curve based on more extensive data would probably show a horizontal asymptote.

The results of the tests described in the foregoing Examples indicate that if quinidine is co-administered with DM, then DM circulation in the blood is increased and prolonged, without causing severe side effects. Accordingly, the co-administration of an anti-oxidant compound such as quinidine in conjunction with DM can increase the effectiveness of DM in any context that depends upon the concentration of DM circulating in the blood, including the activity of DM an antitussive (cough suppressing) agent.

Although this invention has been described with reference to certain specific embodiments, those skilled in the art will recognize that various modifications can be made to those particular embodiments without departing from the spirit or teachings of this invention. Such modifications are considered to be within the scope and coverage of the claims below.

REFERENCES

Albers, G. W., et al, "Safety and tolerance of oral dextromethorphan in patients at risk for brain ischemia," *Stroke* 22: 1075–1077 (1991)

Applebaum, J. S., et al, "Dextromethorphan in the treatment of ALS: A pilot study," Abstract number 960S (page 393) in *Neurology* 41 (Suppl, 1), March 1991

Brinn, R., et al, "Sparteine oxidation is practically abolished in quinidine-treated patients," *Br. J Clin. Pharmacol* 22: 194–197 (1986)

Broly, F., et al, "Effect of quinidine on the dextromethorphan O-methylase activity of microsomal fractions from human liver," *Br. J. Clin. Pharmacol.* 28: 29–36 (1989)

Brosen, K., et al, "Extensive metabolizers of debrisoquin become poor metabolizers during quinidine treatment," *Pharmacol. Toxicol.* 60: 312–314 (1987)

Carpenter, C. L., et al, "Dextromethorphan and dextrorphan as calcium channel antagonists," *Brain Research* 439: 372–375 (1988)

Choi, D. W., "Dextrorphan and dextromethorphan attenuate glutamate neurotoxicity," *Brain Res.* 402: 333–336 (1987)

Craviso, G. L., and Musacchio, J. M., "High affinity dextromethorphan binding sites in guinea pig brain," *Mol. Pharmacol.* 23: 619–640 (1983)

Dayer, R., et al, "Dextromethorphan O-demethylation in liver microsomes . . ."*Clin. Pharmacol. Ther.* 45: 34–40 (1989)

Feeser et al, *Neurosci. Letters* 86: 340–345 (1988)

Ferkany et al, *Eur. J. Pharmacol.* 151: 151–154 (1988)

Fonne-Pfister et al, *Biochem. Biophys. Res. Communic.* 148: 1144–1150 (1987)

Guttendorf, R. J., et al, "Simplified phenotyping with dextromethorphan by thin-layer chromatography: Application to clinical laboratory screening for deficiencies in oxidative drug metabolism," *Ther. Drug. Monit.* 10: 490–498 (1988)

Inaba, T., et al, "In vitro inhibition studies of two isozymes of human liver cytochrome P-450," *Drug Metabolism and Disposition* 13: 443–447 (1985)

Inaba, T., et al, "Quinidine: Potent inhibition of sparteine and debrisoquin oxidation in vivo," *Br. J. Clin. Pharmacol.* 22: 199– 200 (1986)

Koppel, C., et al, "Urinary metabolism of dextromethorphan in man," *Arzneim.-Forsch./Drug Research* 37: 1304–1306 (1987)

Koyuncuoglu & Saydam, *Intnl. J. Clin. Pharmacol. Ther. Tox.* 28: 147–152 (1990)

Kupfer, A., et al, "Dextromethorphan as a safe probe for debrisoquin hydroxylation polymorphism," *Lancet ii:* 517–518 (1984)

Leander, *Epilepsy Res.* 4: 28–33 (1989)

Musacchio, J. M., et al, "High affinity dextromethorphan binding sites in the guinea pig brain," *J. Pharmacol. Exp. Ther.* 247: 424–431 (1988)

Nielsen, M. D., et al, "A dose-effect study of the in vivo inhibitory effect of quinidine on sparteine oxidation in man," *Br. J. Clin. Pharmacol.* 29: 299–304 (1990)

Niznik et al, *Arch. Biochem. Biophys.* 26: 424–432 (1990)

Prince & Feeser, *Neurosci. Letters* 85: 291–296 (1988)

Ramachander, G., et al, "Determination of dextrorphan in plasma and evaluation of bioavialability dextromethorphan hydrobromide in humans," *J Pharm. Sci* 66: 1047–1048 (1977)

Rodd, E. H., *Chemistry of Carbon Compounds* (Elsevier Publ., New York, 1960)

Steinberg, G. K., et al, "Delayed treatment with dextromethorphan and dextrorphan reduces cerebral damage after transient focal ischemia," *Neurosci Letters* 89: 193–197 (1988)

Tortella et al, *TIPS* 10: 501–507 (1989)

Vettican, S. J., et al, "Phenotypic differences in dextromethorphan metabolism," *Pharmaceut Res.* 6: 13–19 (1989)

Walker, E. O., and Hunt, V. P., "An open label trial of dextromethorphan in Huntington's Disease," *Clin. Neuropharmacol* 12: 322–330 (1989)

Wong, B. Y., et al, "Dextrorphan and dextromethorphan, common antitussives, are antiepileptic and antagonize NMDA in brain slices," *Neurosci Letters* 85: 21–26 (1988)

I claim:

1. A method of treating a patient to suppress severe coughing which cannot be suppressed adequately by dextromethorphan alone, comprising administering to a patient in need thereof a combination of dextromethorphan, and a pharmaceutically acceptable second compound which inhibits enzymatic oxidation of dextromethorphan by debrisoquin hydroxylase, wherein the second compound is selected from the group consisting of quinidine, quinine, and salts and isomers thereof.

2. The method of claim 1 wherein quinidine is administered to a patient at a dosage not exceeding about 150 milligrams per day.

3. A method of treating a patient to suppress coughing, comprising administering to a patient who is an extensive metabolizer of dextromethorphan and who is in need of cough suppression a combination of dextromethorphan and a second compound which, in the body of that patient, is pharmaceutically acceptable and causes a significant inhibition of enzymatic oxidation of dextromethorphan by debrisoquin hydroxylase, wherein the second compound is selected from the group consisting of quinidine, quinine, and salts and isomers thereof.

4. The method of claim 3 wherein quinidine is administered to a patient at a dosage not exceeding about 150 milligrams per day.

5. In the method of using dextromethorphan as a cough suppressant, the improvement wherein a patient who is receiving dextromethorphan as a cough suppressant and who is an extensive metabolizer of dextromethorphan also receives a second compound which, in the body of that patient, is pharmaceutically acceptable and causes a significant inhibition of oxidation of dextromethorphan by debrisoquin hydroxylase, and wherein the second compound is selected from the group consisting of quinidine, quinine, and salts and isomers thereof.

6. The method of claim 5 wherein quinidine is administered to a patient at a dosage not exceeding about 150 milligrams per day.

* * * * *